US012661000B2

(12) United States Patent  
Laurenceau et al.

(10) Patent No.: US 12,661,000 B2  
(45) Date of Patent: Jun. 23, 2026

(54) APPARATUS FOR RECOMMENDING AN OPTICAL DEVICE

(71) Applicant: Essilor International, Charenton-le-pont (FR)

(72) Inventors: Berangere Laurenceau, Charenton-le-pont (FR); Didier Grand-Clement, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 714 days.

(21) Appl. No.: 17/905,041

(22) PCT Filed: Mar. 1, 2021

(86) PCT No.: PCT/EP2021/055032
§ 371 (c)(1),
(2) Date: Aug. 25, 2022

(87) PCT Pub. No.: WO2021/170872
PCT Pub. Date: Sep. 2, 2021

(65) Prior Publication Data
US 2023/0097543 A1 Mar. 30, 2023

(30) Foreign Application Priority Data
Feb. 28, 2020 (EP) ..................................... 20305208

(51) Int. Cl.
*A61B 3/00* (2006.01)
(52) U.S. Cl.
CPC .................................. *A61B 3/0025* (2013.01)

(58) Field of Classification Search
CPC ............................ A61B 3/0025; G02C 13/005
See application file for complete search history.

(56) References Cited

U.S. PATENT DOCUMENTS 8,356,896 B2 1/2013 Esser et al.
2003/0107707 A1 6/2003 Fisher et al.
(Continued)

FOREIGN PATENT DOCUMENTS

EP 1 261 273 A1 8/2001
EP 3 539 459 A1 9/2019
(Continued)

OTHER PUBLICATIONS

Combined Chinese Office Action and Search Report issued Jan. 12, 2024 in Chinese Patent Application No. 202180014226.5 (with English Translation), 18 pages.
(Continued)

*Primary Examiner* — Jack Dinh
(74) *Attorney, Agent, or Firm* — Oblon, McClelland, Maier & Neustadt, L.L.P.

(57) ABSTRACT

An apparatus for recommending an optical device adapted to a wearer having a current optical device, the apparatus including processing circuitry that receives and stores measured data relating to features measured on the wearer using at least one measuring instrument, anamnesis data relating to the anamnesis of the wearer, and current optical device data relating to the current optical device used by the wearer, that processes at least two of the measured, anamnesis, and current optical device data based on predetermined processing rules, and that recommends an optical device for the wearer based on the data.

19 Claims, 3 Drawing Sheets

(56)                    References Cited

U.S. PATENT DOCUMENTS

| | | |
|---|---|---|
| 2013/0132898 A1 | 5/2013 | Cuento |
| 2018/0239173 A1 | 8/2018 | Cuento |

FOREIGN PATENT DOCUMENTS

| | | |
|---|---|---|
| JP | 2002-83156 A | 3/2002 |
| JP | 2014-134782 A | 7/2014 |
| WO | WO 2019/075526 A1 | 4/2019 |

OTHER PUBLICATIONS

Office Action issued Apr. 8, 2024, in corresponding Japanese Patent Application No. 2022-548766 (with English Translation), 7 pages.
International Search Report mailed on May 27, 2021 in PCT/EP2021/055032 filed on Mar. 1, 2021, (3 pages).

| | R | | | | L | | | |
|---|---|---|---|---|---|---|---|---|
| | S | C | A | Add | S | C | A | Add |
| Prescription | - 2.73 | - 0.42 | 163° | + 0.25 | - 2.73 | - 0.42 | 163° | + 0.25 |

| | | |
|---|---|---|
| Anti reflect | 🖊 | 🗑 |
| UV protect | 🖊 | 🗑 |
| Progressive lenses | 🖊 | 🗑 |
| ＋ | | |

We recommend progressive lenses because your age > 45

APPARATUS FOR RECOMMENDING AN OPTICAL DEVICE

TECHNICAL FIELD

The invention relates to an apparatus for recommending an optical device adapted to a wearer having a current optical device and to a method for recommending an optical device adapted to a wearer having a current optical device.

BACKGROUND OF THE INVENTION

Usually, a wearer of an optical device wishing to have a new optical device goes to see an eye care practitioner.

The eye care practitioner may use different measuring instruments to make measurements of the wearer, so as for example to determine the ophthalmic prescription of the wearer.

The wearer may answer some questions concerning this vision and/or lifestyle or habit.

Based on the measurements and the answers of the wearer the eye care practitioner using his best practice may recommend an optical device to the wearer.

The current optical device recommendation process presents some drawbacks.

In the recent years, new optical device, in particular ophthalmic lenses with new optical designs have been invented.

These new optical devices are more and more customized according to the wearer.

To determine the optical device the more adapted to the wearer requires more and more wearer data. The gathering and processing of such wearer data is more and more complex.

The wearer may need to go through different measurement instruments in different location and the amount of wearer parameter has become so great that it is more and more complex for an eye care professional to determine the best possible optical device for the wearer.

Furthermore, new optical device are created at a higher frequency, making the recommendation of the most appropriate optical device more and more complex.

Therefore, there is a need for an apparatus and a method to assist an eye care professional in the determination of the most appropriate optical device for a wearer among all the possible optical device and using at best the wearer data available.

An aim of the present invention is to propose such an apparatus and method.

SUMMARY OF THE INVENTION

To this end, the invention proposes an apparatus for recommending an optical device adapted to a wearer having a current optical device, the apparatus comprising processing circuitry configured to:

receive and store:
  measured data relating to features measured on the wearer using at least one measuring instrument,
  anamnesis data relating to the anamnesis of the wearer,
  current optical device data relating to the current optical device used by the wearer, process, for example at least two of, the measured, anamnesis and current optical device data based on predetermined processing rules, and recommend an optical device for the wearer based on the proceed data.

Advantageously, the apparatus according to the invention allows recommending an optical device to a wearer having a current optical device by processing a number of data related to the wearer based on predetermined processing rules so as to help the eye care professional recommend the most adapted optical device to the wearer.

According to further embodiments which can be considered alone or in combination:

the current optical device is the optical device the wearer has been using over a given period of time, for example over the last month, or over the last three months; and/or the measured data relate at least to the prescription of the wearer and/or to the measured refractive sensibility of the wearer and/or the measured ease of accommodation of the wearer and/or the kappa angle; and/or the anamnesis data comprise questions relating at least to the vision habit and/or the vision comfort and/or eye light sensitivity and/or the vision environment and/or the lifestyle of the wearer; and/or the processing circuitry is further configured to receive and store age data relating to the age of the wearer, process such age data together with the measured, anamnesis and current optical device data based at least part of the predetermined processing rules; and/or the processing circuitry is further configured to adapt at least part of the predetermined processing rules based at least on the current optical device data; and/or the processing circuitry allows to customize the recommended optical device; and/or the processing circuitry is further configured to adapt at least part of the predetermined processing rules based at least on the previous customizations; and/or recommendation of an optical device comprises the type of optical device and/or the optical function of the optical device and/or a coating of the optical device; and/or the apparatus further comprises a display device and the processing circuitry is further configured to display a graphic representation of the recommended optical device; and/or the processing circuitry is further configured to display a graphic representation of the impact of the measured and/or anamnesis data on the recommended optical device; and/or the apparatus further comprises a display device and the processing circuitry is further configured to display:
  a gaze distance scale and an indication on said scale
    a range of gaze distances corresponding to the gaze distances at which wearers having similar features as the wearer are comfortable,
    an indication of the gaze distance at which the wearer is comfortable when using his current optical device, and
    upon a selection of the recommended optical device display an indication of the adapted gaze distance at which the wearer is comfortable when using the recommended optical device.

The disclosure further relates to a method performed by processing circuitry of an apparatus for recommending an optical device adapted to a wearer having a current optical device, the method comprising:
  receiving and storing:

3
4 measured data relating to features measured on the wearer using at least one measuring instrument, anamnesis data relating to the anamnesis of the wearer, current optical device data relating to the current optical device used by the wearer, processing, for example at least two of, the measured, anamnesis and current optical device data based on predetermined processing rules, and recommending an optical device for the wearer based on the proceed data.

According to further embodiments which can be considered alone or in combination:

the current optical device is the optical device the wearer has been using over a given period of time, for example over the last month, or over the last three months; and/or the measured data relate at least to the prescription of the wearer and/or to the measured refractive sensibility of the wearer and/or the measured ease of accommodation of the wearer and/or the kappa angle; and/or the anamnesis data comprise questions relating at least to the vision habit and/or the vision comfort and/or eye light sensitivity and/or the vision environment and/or the lifestyle of the wearer; and/or the method further comprises receiving and storing age data relating to the age of the wearer and processing such age data together with the measured, anamnesis and current optical device data based at least part of the predetermined processing rules; and/or the method further comprises adapting at least part of the predetermined processing rules based at least on the current optical device data; and/or the method further comprises customizing the recommended optical device; and/or the method further comprises adapting at least part of the predetermined processing rules based at least on the previous customizations; and/or recommendation of an optical device comprises the type of optical device and/or the optical function of the optical device and/or a coating of the optical device; and/or the method further comprises displaying a graphic representation of the recommended optical device; and/or the method further comprises displaying a graphic representation of the impact of the measured and/or anamnesis data on the recommended optical device; and/or the method further comprises displaying:

a gaze distance scale and an indication on said scale a range of gaze distances corresponding to the gaze distances at which wearers having similar features as the wearer are comfortable, an indication of the gaze distance at which the wearer is comfortable when using his current optical device, and upon a selection of the recommended optical device displaying an indication of the adapted gaze distance at which the wearer is comfortable when using the recommended optical device.

The disclosure further relates to a computer program product comprising one or more stored sequences of instructions that are accessible to a processor and which, when executed by the processor, causes the processor to carry out the steps of the method according to the disclosure.

The disclosure also relates to a computer-readable storage medium having a program recorded thereon; where the program makes the computer execute the method of the disclosure.

Unless specifically stated otherwise, as apparent from the following discussions, it is appreciated that throughout the specification discussions utilizing terms such as "processing", "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, SIM cards, or any other type of media suitable for storing electronic instructions, and capable of being coupled to a computer system bus.

The methods presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below.

In addition, embodiments of the present disclosure are not described with reference to any particular programming language. It will be appreciated that a variety of programming languages may be used to implement the teachings of the disclosure as described herein.

BRIEF DESCRIPTION OF THE DRAWINGS

Non-limiting embodiments of the invention will now be described with reference to the accompanying drawing wherein.

Elements in the figures are illustrated for simplicity and clarity and have not necessarily been drawn to scale. For example, the dimensions of some of the elements in the figure may be exaggerated relative to other elements to help to improve the understanding of the embodiments of the present invention.

DETAILED DESCRIPTION OF EMBODIMENTS OF THE DISCLOSURE

The disclosure relates to an apparatus for recommending an optical device adapted to a wearer having a current optical device.

In the context of the present disclosure, the term "optical device" refers to an any optical equipment that may be worn by a wearer to correct the wearer's vision and/or provide visual protection and/or provide visual information to the wearer.

If the optical device is an optical lens, the recommendation of the optical lens may relate to the optical function of the optical lens and/or the different possible coatings of the optical lens and/or the geometry of the optical lens and/or the material of the optical lens, the mounting parameters when the optical lens is to be mounted in a spectacle frame.

The optical function may comprise dioptric function, light absorption, polarizing capability, reinforcement of contrast capacity, etc. . . . .

The dioptric function corresponds to the optical lens power (mean power, astigmatism etc. . . . ) as a function of the gaze direction.

The optical function of the optical device may comprise the dioptric function of at least one the lenses, a sun protection function for example by controlling a transmission parameter of the optical device or the polarization of a surface of at least one of the lenses that the optical device may comprise.

The optical device may comprise a spectacle optical lens to be mounted on a spectacle frame. The spectacle lens may be solar lens and/or ophthalmic lens.

The optical device may comprise a display head mounted device adapted to display visual information to the wearer.

The apparatus according to the invention comprises processing circuitry configured to receive, and store, for example in a memory, different type of data related to the wearer.

Figure 1:
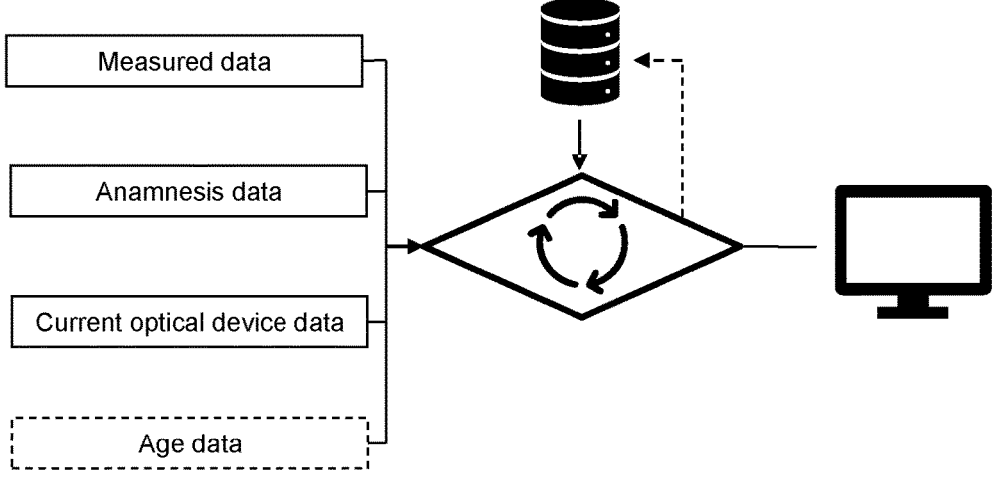
FIG. 1 is a schematic representation of an apparatus according to the present disclosure.

As illustrated on FIG. 1, the processing circuitry may be configured to receive, and store measured data.

The measured data relate to features measured on the wearer using at least one measuring instrument.

The measured data may relate to the prescription of the wearer. The "prescription of the wearer" is to be understood to mean a set of optical characteristics of optical power, of astigmatism, of prismatic deviation, of axis determined by an ophthalmologist or optometrist in order to correct the vision defects of the wearer, for example by means of a lens positioned in front of his eye. For example, the prescription for a myopic eye comprises the values of optical power and of astigmatism with an axis determined for the distance vision.

The prescription of the wearer may be determined using different measuring process such as objective measurements or subjective measurements. The different measured data relating to the prescription of the wearer can be received and stored by the processing circuitry of the apparatus according to the present disclosure.

The measured data may relate to the measure refractive sensibility of the wearer. The refractive sensibility of the wearer may be determined using the method disclosed in the pending patent application WO2020/016398.

The measured data may relate to the measured ease of accommodation of the wearer.

The measured data may relate to the measured kappa angle. The kappa angle being the angle between the pupillary and visual axis.

The measured data by the measuring instrument might enable to determine if the wearer is subject to refraction with addition and/or that the ease of accommodation of the wearer is limited.

As illustrated on FIG. 1, the processing circuitry may be configured to receive and store anamnesis data.

The anamnesis data may relate to the vision case history of the wearer. Such information may be provided either by the wearer himself by answering specific questions, or by other people who know the wearer and can give suitable information, with the aim of obtaining information relating to the vision of the wearer.

The anamnesis data may comprise information relating to the vision habit of the wearer. For example, the allocation of the wearer's time spent gazing a short distance, intermediate distance and far distance.

The anamnesis data may comprise information concerning the vision comfort of the wearer. For example, indication if the wearer is comfortable when reading, looking at a computer screen, a TV screen, driving, walking in the street or down or up stairs.

The anamnesis data may comprise information concerning the eye light sensitivity of the wearer. In particular the sensitivity of the eye of the wearer to intensity and/or wave length of the light.

The anamnesis data may comprise information concerning the vision environment of the wearer. For example, vision environment information may comprise an indication if the environment of the wearer is mostly artificial light or natural light, how long does the wearer use a screen per day, the quantity of UV light in the vision environment of the wearer.

The anamnesis data may comprise information concerning the lifestyle of the wearer. For example, lifestyle information may comprise indications of the daily time spent readying, looking at a screen, inside, outside, driving in the day or at night.

In the present disclosure, anamnesis data are different from prescription data.

As illustrated on FIG. 1, the processing circuitry may be configured to receive and store current optical device data. The current optical device data may relate to the current optical device used by the wearer.

The current optical device may corresponds to the optical worn by the wearer while using the apparatus according to the disclosure.

It is understood by current optical, the optical device use by the wearer in his everyday life.

Current optical device data may be obtained or derived based on the wearer prescription and/or wearer's wearing conditions to be facing the apparatus according to the disclosure. Preferably, the current optical device data may be obtained or derived based on the previous wearer prescription.

Preferably, the previous prescription defines the last prescription provided to the wearer prior to be facing the apparatus according to the disclosure.

In a particular embodiment, a current optical device may be determined by a comparison of numeric values measured on the optical device worn by the wearer and last previous prescription and/or previous wearing conditions data provided to the wearer prior to be facing the apparatus according to the disclosure.

If the difference between the numeric values of the measured optical device measured data and the previous prescription and/or previous wearing conditions data are below a threshold value, the optical device worn by the wearer corresponds to the current optical device provided based on the previous prescription and/or previous wearing conditions data.

Preferably, the measured the previous prescription and/or previous wearing conditions data are stored in a database.

The current optical device data may relate to the optical function of the current optical lens and/or the different coatings of the current optical lens and/or the geometry of the current optical lens and/or the material of the current optical lens, the current mounting parameters if the current optical lens is mounted in a spectacle frame.

Advantageously, the current optical device data may be used to better understand and interpret some of the anamnesis answers.

For example, knowing if the current optical device used by the wearer has a blue light protection coating may be relevant when interpreting answers of the wearer concerning his comfort when using a computer or watching TV.

Furthermore, knowing if the current optical device has progressive additional lens may be useful when using recommending a new optical device.

As illustrated on FIG. 1, the processing circuitry may be configured to receive and store age data relating to the age of the wearer.

As illustrated on FIG. 1, the processing circuitry is further configured to process, for example at least two of, the measured, anamnesis and current optical device data based on predetermined processing rules.

In a preferred embodiment, the processing circuitry is further configured to process all of the measured, anamnesis and current optical device data based on predetermined processing rules.

The predetermining processing rules, may help the eye care professional process all the data that may be gathered concerning the vision of the wearer. Indeed, with the increase of available data, the increase customization of optical equipment and the increase accuracy of possible measurements and provided optical device it because more and more difficult for an eye care professional to manually or mentally process all available information.

A processing rule is an algorithm that takes into account different data received by the apparatus according to the disclosure among a non exhaustive list before to determine and give recommendation of an optical device that suits the wearer's needs, therefore, assisting the eye care professional in the recommendation to make to the wearer.

It is known by the person skilled in the art wearer data, geographic area of the wearer and any optical defects measured have an influence on the optical device to recommend to the wearer.

The non exhaustive list may comprise the type of the current optical device, the prescription of the current optical device, the age, the sex of the wearer, the geographic origin of the wearer, any optical defect such as limited east to accomplish accommodation, refraction with addition and/or eye strain.

These data are non-exhaustive examples of data which could be considered by the proceeding rules to proceed to optical device recommendation.

Based on the data received by the apparatus according to the disclosure, different processing rules apply to recommend an optical element adapted to the wearer.

The predetermined processing rules may be selected or given different weight based on the current optical device of the wearer.

The interpretation of certain visual discomfort or comfort of the wearer may be process differently depending on the current optical equipment of the wearer.

For example, anti-reflective coating is known to reduce visual discomfort when driving at night. Therefore, a wearer having on his current optical device an anti-reflective coating may not indicate any visual discomfort when driving at night, nevertheless, the predetermined processing rules should recommend an anti-reflective coating.

All other things being equal the recommendation of the optical equipment is different when the current equipment of the wearer comprises progressive addition lens or not.

As illustrated on FIG. 1, the processing circuitry is further configured to recommend an optical device for the wearer based on the proceed data.

The recommendation may relate to any of the type of optical device, such as but not limited to corrective lens and/or protective lens, single vision, reading lens, progressive addition lens, multifocal lens.

The recommendation may further relate to the optical function of an optical lens comprised in the optical device or being the optical device.

The recommendation may further relate to coating of the optical device such as but not limited to hard coat, self-healing coating, anti-reflective coating, blue light filter coating.

As illustrated on FIG. 1, the apparatus of the present disclosure may further allow for customizing the recommended optical device. For example, the eye care professional may adapt the recommendation based on his best practice.

According to an embodiment of the invention, the apparatus according to the present disclosure may be further configured to adapt at least part of the predetermined processing rules based at least on the previous customizations.

Advantageously, the predetermined processing rules may adapt to the best practice of an eye care professional reducing the need for said professional to adapt his recommendations.

Optionally, upon adaptation of the recommendation the eye care professional may be asked if such recommendation is to be taken into account in the predetermined processing rules.

Advantageously, the apparatus of the disclosure avoids multiple data entry, subsequent errors, reduces paper files and the need for storage space. Streamlining the eye care professional practice and data-sharing is made easier.

The apparatus of the disclosure helps accelerate the eye care professional workflow productivity by creating a smooth wearer journey in the eye care professional store.

Improving the in-store workflow empowers the eye care professional to deliver a higher quality of wearer care.

The apparatus according to the present disclosure has the capability to securely store the collected data over many years. Wearer history such as instrument data, prescriptions and lens recommendation may be available instantaneously, allowing the eye care professional to compare historic and current results. In addition, the eye care professional data may be automatically backed up to safely secure all information.

As illustrated on FIG. 1, the apparatus of the present disclosure may further comprise a display device and the processing circuitry may be further configured to display a graphic representation of the recommended optical device.

Figure 2:
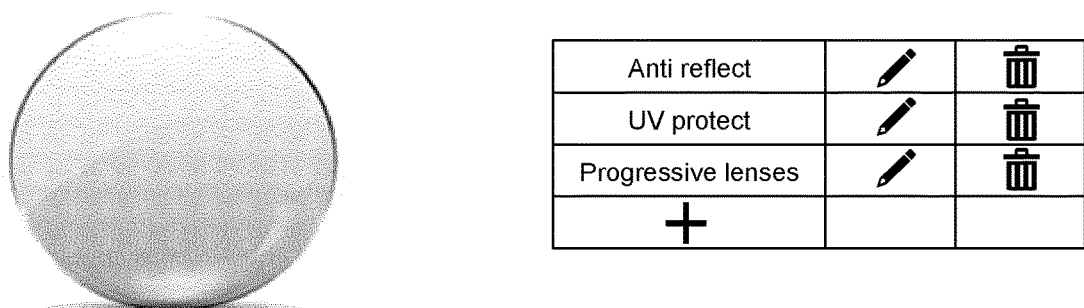
FIG. 2 is an example of a display of a recommended optical device.

FIG. 2 is an illustrative example of such graphic representation of a recommended optical lens.

According to an embodiment of the disclosure the processing circuitry is further configured to display a graphic representation of the impact of the measured and/or anamnesis data on the recommended optical device.

Advantageously, the apparatus according to the present disclosure may help the eye care professional fully engage the wearer.

The apparatus of the present disclosure may help organize and highlight the relevant information all along the eye exam, starting with a digital anamnesis, the apparatus of the present invention allows an eye care professional to be more impactful when presenting to the wearer personal visual data and needs.

According to an embodiment of the present disclosure, the apparatus further comprises a display device and the processing circuitry is further configured to display:

a gaze distance scale and an indication on said scale a range of gaze distances corresponding to the gaze distances at which wearers having similar features as the wearer are comfortable, an indication of the gaze distance at which the wearer is comfortable when using his current optical device, and upon a selection of the recommended optical device display an indication of the adapted gaze distance at which the wearer is comfortable when using the recommended optical device.

Figure 3:
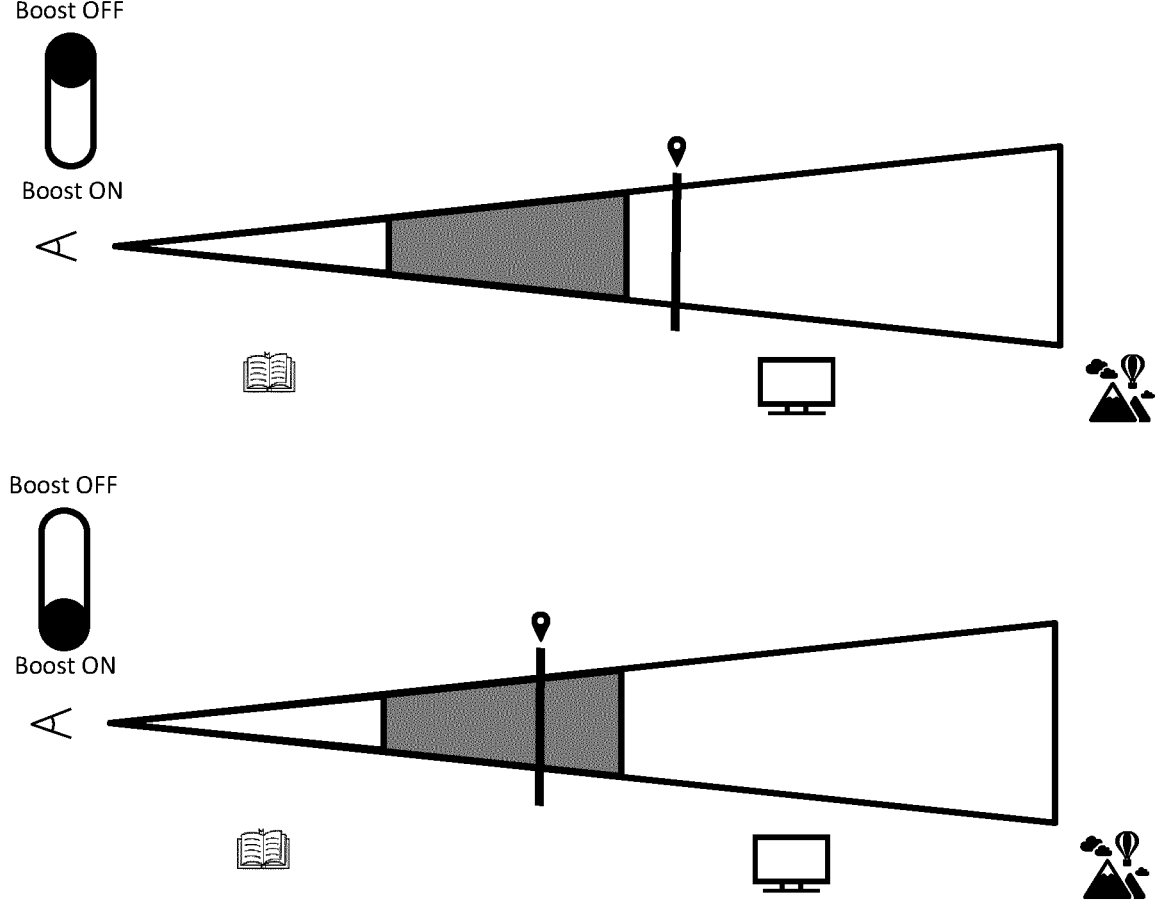
FIG. 3 is an example of a display illustrating the effect of a optical device on the visual comfort of the wearer.

An example of such display is illustrated on FIG. 3.

Advantageously, such representation of the result of the recommended optical device, helps the wearer understand the gain of the recommended optical device.

Indeed, by simply selecting the recommended optical device, the eyecare professional may show the wearer that the gaze direction at which he will be comfortable has changed and is within the range of wearers having similar features, such as the same age and/or the same vision issues.

Figure 4:
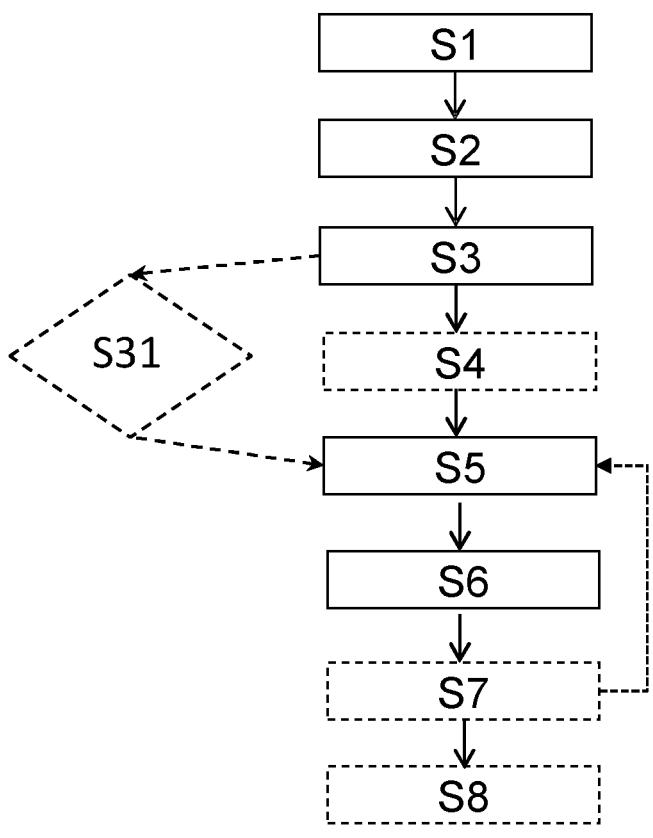
FIG. 4 is a flow chart representing a method according to the present disclosure.

As illustrated on FIG. 4, the present disclosure further relates to a method performed by processing circuitry of an apparatus for recommending an optical device adapted to a wearer having a current optical device.

The method of the present disclosure may comprise a step S1 of receiving and storing measured data relating to features measured on the wearer using at least one measuring instrument.

The detail description of the measured data in relation to the apparatus of the present disclosure apply to the method according to the present disclosure.

The method of the present disclosure may comprise a step S2 of receiving and storing anamnesis data relating to the anamnesis of the wearer.

The detail description of the anamnesis data in relation to the apparatus of the present disclosure apply to the method according to the present disclosure.

The method of the present disclosure may comprise a step S3 of receiving and storing current optical device data relating to the current optical device used by the wearer.

The detail description of the current optical device data in relation to the apparatus of the present disclosure apply to the method according to the present disclosure.

The method of the present disclosure comprises a step S5 of processing at least two of, preferably of all of, the measured, anamnesis and current optical device data based on predetermined processing rules.

The detail description of the processing in relation to the apparatus of the present disclosure apply to the method according to the present disclosure.

As illustrated on FIG. 4, the method of the present disclosure comprises a step S6 of recommending an optical device for the wearer based on the proceed data.

The detail description of the recommendation in relation to the apparatus of the present disclosure apply to the method according to the present disclosure.

Optionally, the method of the present disclosure may comprise a step S4 of age data relating to the age of the wearer and processing such age data together with the measured, anamnesis and current optical device data based at least part of the predetermined processing rules.

The detail description of the age data in relation to the apparatus of the present disclosure apply to the method according to the present disclosure.

As illustrated on FIG. 4, the method of the present disclosure may comprise a step S31 of adapting at least part of the predetermined processing rules based at least on the current optical device data.

The detail description of the adaptation of the predetermined processing rules based on the current optical device data in relation to the apparatus of the present disclosure apply to the method according to the present disclosure.

In addition to the step of recommending an optical device, the method of the present disclosure may comprise a step S7 of customizing the recommended optical device.

As illustrated on FIG. 4, at least part of the predetermined processing rules may be adapted based on the customizations issued from step S7.

The detail description of the customization of the recommendation and the adaptation of the predetermined processing rules in relation to the apparatus of the present disclosure apply to the method according to the present disclosure.

Preferably, the method of the present disclosure comprises a step S8 of displaying a graphic representation of the recommended optical device.

The method of the invention may further comprise a step of displaying a graphic representation of the impact of the measured and/or anamnesis data on the recommended optical device.

The detail description of the display of the recommendation and the impact of the measured and/or anamnesis data on the recommended optical device in relation to the apparatus of the present disclosure apply to the method according to the present disclosure.

According to an embodiment of the present disclosure, the method may comprise displaying:

a gaze distance scale and an indication on said scale a range of gaze distances corresponding to the gaze distances at which wearers having similar features as the wearer are comfortable, an indication of the gaze distance at which the wearer is comfortable when using his current optical device, and upon a selection of the recommended optical device displaying an indication of the adapted gaze distance at which the wearer is comfortable when using the recommended optical device.

Although presented in a certain order, the different steps of the method according to the present disclosure can be executed in a different order depending on the needs of the eye care professional. In particular, the step S1 to S4 may be executed in any order as preferred by the eye care professional carrying out the method of the present disclosure.

EXAMPLES

Example 1

A wearer has single vision lenses as current optical device. In the last wearer's anamnesis, the wearer indicates having eye strain when he is reading.

Based on a measurement by the measuring instrument, the apparatus according to the disclosure determines that the wearer's ease of eye accommodation is limited.

In the present example, the apparatus for recommending an optical device receives three inputs:

the current optical device being progressive lenses,

the anamnesis referring to eye strain when reading, and measure of a limited wearer's ease of eye accommodation.

Based on these inputs, the apparatus determines that the eye care professional should recommend an optical lens being single vision lenses having an optical power boost to enhance the wearer's near vision and could enable to overcome the limited ease for accommodation and could enable to overcome the limited ease for accommodation.

Based on these inputs, the apparatus recommends replacing the progressive lenses, being the current optical device of the wearer, by a single vision optical lenses having an optical power boost.

Example 2

A wearer has single vision lenses as current optical device. In the last wearer's anamnesis, the wearer indicates having no eye strain when he is reading.

Based on a measurement by the measuring instrument, the apparatus according to the disclosure determines that the wearer's is not subject to refraction with addition and the ease of eye accommodation is not limited.

In the present example, the apparatus for recommending an optical device receives four inputs:

the current optical device being single vision lenses,
the anamnesis referring to no eye strain when reading,
the wearer is not subject to refraction with addition, and
no limited wearer's ease of eye accommodation is measured.

Based on these inputs, the apparatus determines that the eye care professional should still recommend an optical lens being single vision lenses, as no vision defect has been measured by the measuring instrument or provided by the anamnesis.

Based on these inputs, the apparatus recommends the wearer to keep using single vision optical lenses.

Example 3

A wearer has single vision lenses as current optical device. In the last wearer's anamnesis, the wearer indicates having eye strain when he is reading.

Based on a measurement by the measuring instrument, the apparatus according to the disclosure determines that the wearer's is not subject to refraction with addition and the ease of eye accommodation is not limited.

In the present example, the apparatus for recommending an optical device receives five inputs:

the current optical device being single vision lenses,
the anamnesis referring to eye strain when reading,
the wearer is not subject to refraction with addition, and
no limited wearer's ease of eye accommodation is measured,
the age of the wearer.

Based on these inputs, the apparatus determines that the eye care professional should recommend an optical lens being single vision lenses having an optical power boost to enhance the wearer's near vision and avoid eye strain when reading.

Based on these inputs, the apparatus recommends replacing the single vision lens, being the current optical device of the wearer, by a single vision optical lenses having an optical power boost to enhance the wearer's near vision.

Example 4

A wearer has single vision lenses as current optical device.

Based on a measurement by the measuring instrument, the apparatus according to the disclosure determines that the wearer's is not subject to refraction with addition but that the ease of eye accommodation is limited.

In the present example, the apparatus for recommending an optical device receives three inputs:

the current optical device being single vision lenses,
the wearer is not subject to refraction with addition, and
limited wearer's ease of eye accommodation is measured.

Based on these inputs, the apparatus determines that the eye care professional should recommend an optical lens being single vision lenses having an optical power boost to enhance the wearer's near vision and could enable to overcome the limited ease for accommodation.

Based on these inputs, the apparatus recommends replacing the single vision lenses, being the current optical device of the wearer, by a single vision optical lenses having an optical power boost.

Example 5

A wearer has single vision lenses as current optical device.

Based on a measurement by the measuring instrument, the apparatus according to the disclosure determines that the wearer's is subject to refraction with addition.

In the present example, the apparatus for recommending an optical device receives two inputs:

the current optical device being single vision lenses, and
the wearer is subject to refraction with addition.

Based on these inputs, the apparatus determines that the eye care professional should recommend an optical lens being progressive lenses to overcome the refraction.

Based on these inputs, the apparatus recommends replacing the single vision lenses, being the current optical device of the wearer, by a progressive lens.

Example 6

A wearer has single vision lenses having an optical power boost as current optical device.

Based on a measurement by the measuring instrument, the apparatus according to the disclosure determines that the wearer's is subject to refraction with addition.

In the present example, the apparatus for recommending an optical device receives three inputs:

the current optical device being single vision lenses having an optical power boost, and
the wearer is subject to refraction with addition.

Based on these inputs, the apparatus determines that the eye care professional should recommend an optical lens being progressive lenses to overcome the refraction.

Based on these inputs, the apparatus recommends replacing the single vision lenses having an optical power boost, being the current optical device of the wearer, by a progressive lens.

Example 7

A wearer has single vision lenses having an optical power boost as current optical device.

Based on a measurement by the measuring instrument, the apparatus according to the disclosure determines that the wearer's is not subject to refraction with addition.

In the present example, the apparatus for recommending an optical device receives three inputs:

the current optical device being single vision lenses having an optical power boost, and the wearer is not subject to refraction with addition.

Based on these inputs, the apparatus determines that the eye care professional should still recommend an optical lens being single vision lenses having an optical power boost, as no vision defect has been measured by the measuring instrument.

Based on these inputs, the apparatus recommends the wearer to keep using single vision optical lenses having an optical power boost.

The above examples define different examples of processing rules.

Other data received by the apparatus according to the invention may lead to this same recommendation. The data received by the apparatus may comprise more or less data, and these data may be the same and/or different the received data of the examples above.

These adaptable recommendations are done thanks to the processing circuitry of the apparatus according to the disclosure.

The invention has been described above with the aid of embodiments without limitation of the general inventive concept.

Many further modifications and variations will be apparent to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. An apparatus for recommending an optical device adapted to a wearer having a current optical device, the apparatus comprising:

processing circuitry configured to:

receive and store input data including:

measured data relating to features measured on the wearer using at least one measuring instrument, anamnesis data relating to the anamnesis of the wearer, and current optical device data relating to the current optical device used by the wearer, process at least two of the measured, anamnesis, and current optical device data based on predetermined processing rules, wherein at least one processing rule of the predetermined processing rules is an algorithm that takes into account different received data to determine and give recommendation of an optical device that suits the wearer's needs, and that assists an eye care professional in the recommendation to make to the wearer, said input data being at least one of a type of the current optical device, a prescription of the current optical device, age, sex of the wearer, geographic origin of the wearer, refraction with addition and/or eye strain, and recommend an optical device for the wearer based on the input data.

2. The apparatus according to claim 1, wherein the measured data relate at least to a prescription of the wearer and/or to measured refractive sensibility of the wearer and/or measured ease of accommodation of the wearer and/or a kappa angle.

3. The apparatus according to claim 2, wherein the anamnesis data comprise questions relating at least to a vision habit and/or a vision comfort and/or eye light sensitivity and/or the vision environment and/or a lifestyle of the wearer.

4. The apparatus according to claim 1, wherein the anamnesis data comprise questions relating at least to a vision habit and/or a vision comfort and/or eye light sensitivity and/or the vision environment and/or a lifestyle of the wearer.

5. The apparatus according to claim 1, wherein the processing circuitry is further configured to receive and store age data relating to the age of the wearer, process such age data together with the measured, anamnesis and current optical device data based at least part of the predetermined processing rules.

6. The apparatus according to claim 1, wherein the processing circuitry is further configured to adapt at least part of the predetermined processing rules based at least on the current optical device data.

7. The apparatus according to claim 1, wherein the processing circuitry allows to customize the recommended optical device.

8. The apparatus according to claim 7, wherein the processing circuitry is further configured to adapt at least part of the predetermined processing rules based at least on previous customizations.

9. The apparatus according to claim 1, wherein recommendation of an optical device comprises type of optical device and/or optical function of the optical device and/or a coating of the optical device.

10. The apparatus according to claim 1, further comprising a display device and the processing circuitry is further configured to display a graphic representation of the recommended optical device.

11. The apparatus according to claim 10, wherein the processing circuitry is further configured to display a graphic representation of the impact of the measured and/or anamnesis data on the recommended optical device.

12. The apparatus according to claim 1, further comprising a display device, wherein the processing circuitry is further configured to display:

a gaze distance scale and an indication on said scale a range of gaze distances corresponding to the gaze distances at which wearers having similar features as the wearer are comfortable, an indication of the gaze distance at which the wearer is comfortable when using his current optical device, and upon a selection of the recommended optical device display an indication of the adapted gaze distance at which the wearer is comfortable when using the recommended optical device.

13. A method performed by processing circuitry of an apparatus for recommending an optical device adapted to a wearer having a current optical device, the method comprising:

receiving and storing input data including:

measured data relating to features measured on the wearer using at least one measuring instrument, anamnesis data relating to the anamnesis of the wearer, and current optical device data relating to the current optical device used by the wearer;

processing at least two of the measured, anamnesis, and current optical device data based on predetermined processing rules, wherein at least one processing rule of the predetermined processing rules is an algorithm that takes into account different received data to determine and give recommendation of an optical device that suits the wearer's needs, and that assists an eye care professional in the recommendation to make to the wearer, said input data being at least one of a type of the current optical device, a prescription of the current optical device, age, sex of the wearer, geographic origin of the wearer, refraction with addition and/or eye strain; and recommending an optical device for the wearer based on the input data.

14. The method according to claim 13, wherein the measured data relate at least to a prescription of the wearer and/or to measured refractive sensibility of the wearer and/or measured ease of accommodation of the wearer and/or a kappa angle.

15. The method according to claim 14, wherein the anamnesis data comprise questions relating at least to a vision habit and/or a vision comfort and/or eye light sensitivity and/or the vision environment and/or a lifestyle of the wearer.

16. A non-transitory computer-readable storage medium including computer executable instructions, wherein the instructions, when executed by a computer, cause the computer to perform a method according to claim 14.

17. The method according to claim 13, wherein the anamnesis data comprise questions relating at least to a vision habit and/or a vision comfort and/or eye light sensitivity and/or the vision environment and/or a lifestyle of the wearer.

18. A non-transitory computer-readable storage medium including computer executable instructions, wherein the instructions, when executed by a computer, cause the computer to perform a method according to claim 17.

19. A non-transitory computer-readable storage medium including computer executable instructions, wherein the instructions, when executed by a computer, cause the computer to perform a method according to claim 13.

* * * * *